United States Patent [19]

Moon et al.

[11] Patent Number: 5,654,321
[45] Date of Patent: Aug. 5, 1997

[54] 2-CHLORO-3-ARYLAMINO-1,4-NAPHTHOQUINONE DERIVATIVES, PROCESS FOR PREPARATION THEREOF AND USE THEREOF AS AN AGENT FOR INHIBITING PLATELET AGGREGATION

[75] Inventors: Chang-Kiu Moon; Chung-Kyu Ryu, both of Seoul, Rep. of Korea

[73] Assignee: Dong Kook Pharmaceutical Co. Ltd., Seoul, Rep. of Korea

[21] Appl. No.: 593,887

[22] Filed: Jan. 30, 1996

[51] Int. Cl.⁶ .......................... C07D 213/02; A61K 31/44
[52] U.S. Cl. .......................... 514/344; 546/289; 546/310; 546/312; 558/414; 514/352; 514/522
[58] Field of Search .......................... 546/289, 310, 546/312; 555/414; 514/344, 352, 522

[56] References Cited

U.S. PATENT DOCUMENTS 4,393,075   7/1983   Terao et al. .......................... 424/304
5,534,536   7/1996   Ohuchida et al. .......................... 514/397

*Primary Examiner*—Zinna Northington Davis
*Attorney, Agent, or Firm*—Oblon, Spivak, McClelland, Maier & Neustadt, P.C.

[57] ABSTRACT

The present invention relates to a novel 2-chloro-3-arylamino-1,4-naphthoquinone derivative represented by the following formula (I), which has a potent inhibitory activity against platelet aggregation:

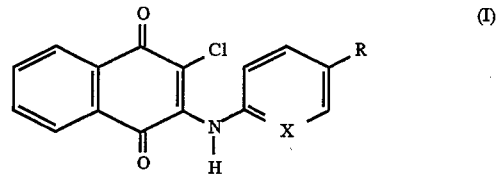

in which
  X represents nitrogen (N) or carbon (C) atom and
  R represents cyano, or
  R can further represent alkyl, carboxyl or acyl when X represents nitrogen (N) atom,
and to a process for preparing thereof and to a pharmaceutical composition for inhibiting blood coagulation which comprises the compound of formula (I) as an active ingredient.

13 Claims, 3 Drawing Sheets

2-CHLORO-3-ARYLAMINO-1,4-NAPHTHOQUINONE DERIVATIVES, PROCESS FOR PREPARATION THEREOF AND USE THEREOF AS AN AGENT FOR INHIBITING PLATELET AGGREGATION

BACKGROUND OF THE INVENTION

1. Field of the Invention

The present invention relates to a novel 1,4-naphthoquinone derivative having a potent inhibitory activity against platelet aggregation. More specifically, the present invention relates to a novel 2-chloro-3-arylamino-1,4-naphthoquinone derivative represented by the following formula (I), which has a potent activity for inhibition of platelet aggregation and therefore, can be used as an agent for inhibition of blood coagulation and for treatment of thrombosis:

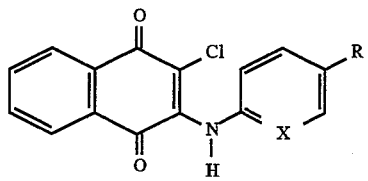

in which

X represents nitrogen (N) or carbon (C) atom and

R represents cyano, or

R can further represent alkyl, carboxyl or acyl when X represents nitrogen (N) atom.

The present invention also relates to a process for preparation of the compound of formula (I), as defined above, and to a pharmaceutical composition for inhibition of blood coagulation which comprises the compound of formula (I) as an active ingredient.

2. Background Art

Platelets occupy the most small part of the cells constituting blood but are easy to respond even to any minute stimulus and therefore, play an important role in maintenance of biological homeostasis, for example, in blood coagulation. Further, the abnormality of platelet aggregation caused by a change in platelet function is one of the major negative factors responsible to blood rheology and thus can cause the abnormal hemostatic mechanism or microcirculation disorder. Particularly, it has been reported that the major cause of interruption in blood circulation which is frequently developed in geriatric diseases such as hypertension, arteriosclerosis, etc., and metabolic disorders such as diabetes mellitus, etc., which have been rapidly increased in modern society, is the abnormal acceleration of platelet aggregation. Accordingly, it has been expected that such related diseases can treat or prevent by normalizing the function of platelets.

1,4-Naphthoquinone derivatives generally have various pharmacological activities such as antimicrobial activity, antifungal activity, anticancer activity, anticoagulant activity, etc., and therefore, have been widely used as the leading compound for development of novel medicinal agents in the field of anticancer and antimicrobial agents. According to the result of numerous studies, it has been reported that vitamin $K_3$ (menadione), which is one of the 1,4-naphthoquinone derivatives, has an effect on inhibition of platelet aggregation in human being. However, the mechanism of vitamin $K_3$ for inhibition of platelet aggregation has not been clearly established yet (see, Blackwell, G. J., Radomski, M. and Moncada, S. Inhibition of human platelet aggregation by vitamin K. Thromb. Res. 37, 103–114, 1985). In addition, it has been disclosed that 2-chloro-3-methyl-1,4-naphthoquinone (CMN) inhibits the platelet aggregation in rabbit by inhibiting the metabolic pathway of phospholipids involving various platelet agonists (see, Ko, F. N., Sheu, S. J., Liu, Y. M., Huang, T. F. and Teng, C. M., Inhibition of rabbit platelet aggregation by 1,4-naphthoquinones, Thromb. Res. 57, 453–463, 1990).

Thus, the present inventors have synthesized various 1,4-naphthoquinone derivatives and examined their activity for inhibition of platelet aggregation. As a result, we have identified that a certain 1,4-naphthoquinone derivative having a different structure from those of presently known 1,4-naphthoquinone derivatives shows a potent activity for inhibition of platelet aggregation, and thus completed the present invention.

Therefore, it is an object of the present invention to provide a novel 2-chloro-3-arylamino-1,4-naphthoquinone derivative of formula (I), as defined above, which has a potent activity for inhibition of platelet aggregation.

It is another object of the present invention to provide a process for preparing the compound of formula (I).

It is a further object of the present invention to provide a pharmaceutical composition for inhibition of platelet aggregation, which comprises the compound of formula (I) as an active ingredient.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention and drawings, in addition to the scope of the invention defined by the claims.

BRIEF DESCRIPTION OF DRAWINGS

For a thorough understanding of the nature and objects of the invention, reference should be had to the following detailed description taken in connection with the accompanying drawings in which.

DISCLOSE OF INVENTION

Figure 2:
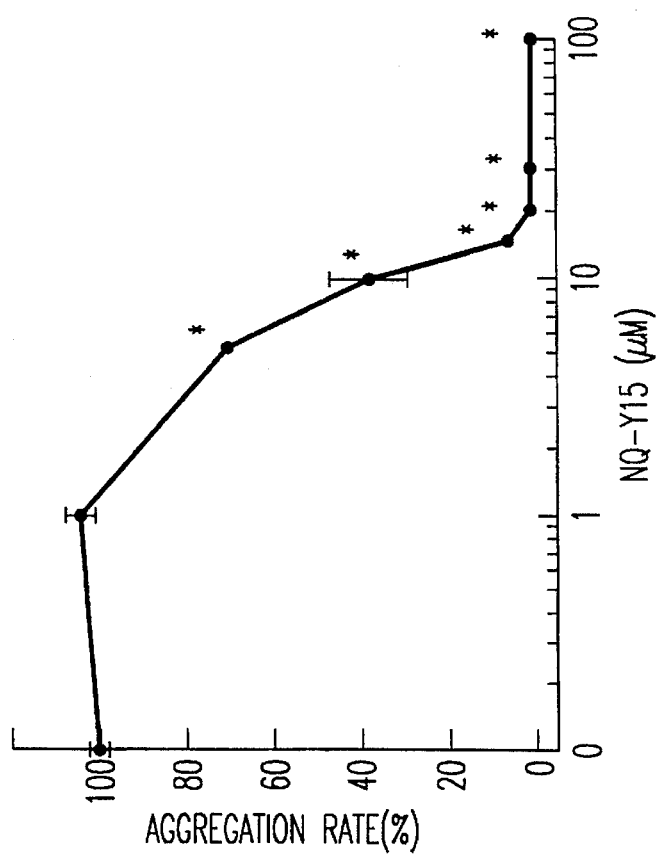
FIG. 2 is a graph showing the inhibitory activity of the compound (NQ-Y15) according to the present invention against platelet aggregation activated by collagen.

In one aspect, the present invention relates to a novel 2-chloro-3-arylamino-1,4-naphthoquinone derivative represented by the following formula (I):

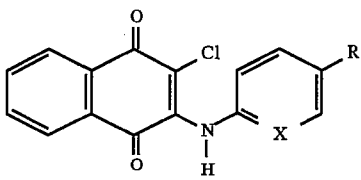

in which

X represents nitrogen (N) or carbon (C) atom and

R represents cyano, or

R can further represent alkyl, carboxyl or acyl when X represents nitrogen (N) atom.

Among the compound of formula (I) according to the present invention, the preferred one includes those wherein X represents nitrogen or carbon atom and R represents cyano, or X represents nitrogen atom and R represents lower alkyl having 1 to 6 carbon atoms, carboxyl or aliphatic acyl group, for example, alkylcarbonyl having 1 to 6 carbon atoms in alkyl moiety.

More preferable compound of formula (I) according to the present invention includes those wherein X represents nitrogen or carbon atom and R represents cyano, or X represents nitrogen atom and R represents methyl, carboxyl or acetyl.

As the particularly preferred one of the compound of formula (I) according to the present invention, the following can be mentioned:

2-chloro-3-[(4-cyanophenyl)-amino]-1,4-naphthoquinone, and 2-chloro-3-[(5-methylpyridin-2-yl)-amino]-1,4-naphthoquinone.

In another aspect, the present invention relates to a process for preparing the novel 2-chloro-3-arylamino-1,4-naphthoquinone derivative of formula (I).

According to the present invention, the 2-chloro-3-arylamino-1,4-naphthoquinone derivative of formula (I) can be prepared by reacting 2,3-dichloro-1,4-naphthoquinone of formula (II) with an arylamine of formula (III). The process according to the present invention can be represented by the following reaction scheme.

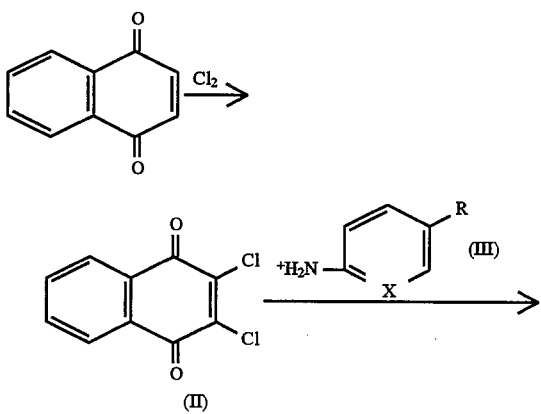

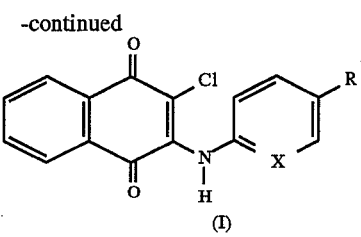

In the above reaction scheme, X and R are defined as previously described.

2,3-Dichloro-1,4-naphthoquinone (DNQ) of formula (II) which is used as the starting material in the process of the present invention is a known compound in this technical field and can be conveniently prepared by reacting 1,4-naphthoquinone with chlorine gas ($Cl_2$).

According to the process of the present invention, DNQ of formula (II) is reacted with the arylamine derivative of formula (III) in the presence of an alcohol solvent to prepare the compound of formula (I). As the alcohol solvent for this reaction, a lower alkanol solvent having 1 to 6 carbon atoms such as methanol, ethanol, propanol, isopropanol, butanol, etc., can be preferably used, with ethanol being particularly preferable.

This reaction can be conducted generally at the temperature between room temperature and 100° C., preferably at boiling point of the solvent used therein under refluxing. The reaction time is generally 2 to 6 hours, preferably 3 to 5 hours.

After the reaction is completed, if necessary, the resulting compound of formula (I) can be separated and purified according to conventional working-up procedures, for example, recrystallization, chromatography, etc.

As mentioned above, the compound of formula (I) according to the present invention has a potent inhibitory activity against platelet aggregation, and therefore, can be effectively used as an agent for inhibition of blood coagulation and for treatment of thrombosis in clinical field.

It has been known that the platelet aggregation is greatly influenced by secretion from platelet granules and by process of secretion and metabolism of arachidonic acid in platelet. Specifically, contrary to other cells, platelets contain numerous granules such as dense granule, α-granule, lysosome and peroxisome, each of which preserves very useful physiological substances. When platelet is activated by any stimulus, substances contained in granules are secreted out of the cells through exocytosis. Particularly, dense granule contains adenine nucleotides such as ADP (adenosine diphosphate), ATP (adenosine triphosphate), etc, calcium, serotonin, etc., which are secreted upon aggregation of platelets and then cause irreversible secondary aggregation. Thus, it can be said that irreversible secondary aggregation induced by ADP, thrombin, etc. is the result of such granule secretion. As can be demonstrated by the following experiments, the compound according to the present invention shows the inhibitory activity against platelet aggregation by inhibiting the platelet aggregation ability and granule secretion of physiologically active substances as mentioned above.

Meanwhile, $PLA_2$(phospholipase $A_2$) of which the activity increases in activated platelet liberates arachidonic acid from phospholipids present in platelet membrane such as phosphatidylcholine, phosphatidylethanolamine, phosphatidylinositol, etc. The liberated arachidonic acid produces prostaglandin $G_2$ and prostaglandin $H_2$, as prostaglandin endoperoxide intermediates, which are present during an extremely short period, by the action of cyclooxygenase. These endoperoxides have a potent inhibitory activity against platelet aggregation but are very unstable substances. Therefore, they produce thromboxane $A_2(TXA_2)$ having the most potent platelet aggregation activity by the action of thromboxane synthetase. Thromboxane $A_2$ activates platelets even at an extremely low-concentration (below 0.1 μM) through increase in platelet adhesiveness, induction of change in platelet shape, reduction in production of cyclic adenosine monophosphate (cAMP) by inhibition of adenylate cyclase, increase in calcium concentration in platelet, overexposure of fibrinogen receptor, and the like to cause the irreversible mass aggregation. As can be demonstrated from the following experiments, it has been identified that the compound according to the present invention contributes to the inhibition of platelet aggregation through the mechanism of inhibiting the synthesis of thromboxane $A_2$ in activated platelets.

As mentioned above, the desired compound of formula (I) according to the present invention shows a potent inhibitory activity against platelet aggregation, and therefore, can be used as an agent useful for inhibition of blood coagulation and treatment of thrombosis. When the compound of formula (I) according to the present invention is clinically used, this active compound can be formulated in various preparations conventionally used in pharmaceutical field, for example, preparations for oral administration such as tablet, capsule, troche, solution, suspension, etc., injectable preparations such as injectable solution or suspension, ready-to-use injectable dry powder which can be reconstituted with injectable distilled water when it is used, etc., topical preparations such as ointment, cream, solution, etc., and the like, according to the conventional method using pharmaceutically acceptable carriers.

The carrier which can be used for this purpose is a conventional one in pharmaceutical field and is, for example, binder, lubricant, disintegrant, excipient, solubilizing agent, dispersing agent, stabilizer, suspending agent, coloring agent, perfume, etc., in the case of oral preparations; preservative, analgesia, solubilizing agent, stabilizer, etc., in the case of injectable preparations; and base, excipient, lubricant, preservative, etc., in the case of topical preparations. The pharmaceutical preparations thus prepared can be administered via oral route or parenteral route, for example, intravenous, subcutaneous or intraperitoneal injection, or can be topically applied. In addition, to prevent decomposition of drugs with gastric acid at the time of oral administration it may be preferable to administer the pharmaceutical preparation together with an antacid or to formulate the oral preparation such as tablet into an enteric-coated preparation.

Although a suitable dosage of the desired 2-chloro-3-arylamino- 1,4-naphthoquinone derivative of formula (I) according to the present invention can be appropriately determined depending on various factors including absorption, inactivation and excretion of the respective active compound in human body, age, sex and condition of subject patients, condition and severity of diseases to be treated, and the like, the Compound of formula (I) can be administered generally in an amount of 5 mg to 35 mg per day, preferably in an amount of 10 mg to 25 mg per day, to adult human being. However, it should be understood that the dosage to be administered can be appropriately reduced or increased depending on individual requirement and decision of physicians based on condition of individual patient and complications by means of a specialized manner. The daily dosage of the active compound can be administered once a day or in multiply divided amount preferably over 3 to 6 times.

The present invention will be more specifically illustrated by the following examples and experiments. However, it should be understood that the present invention is not limited to those examples in any manner.

EXAMPLE 1

Preparation of 2-chloro-3-[(4-cyanophenyl)-amino]-1,4-naphthoquinone

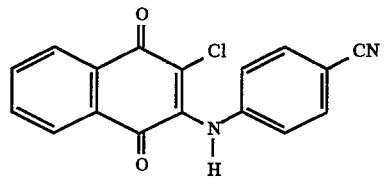

(1) 20 g of 1,4-naphthoquinone was dissolved in 200 ml of acetic acid and about 10 g of chlorine ($Cl_2$) gas was introduced into the resulting solution. The reaction mixture was agitated for 4 hours at room temperature, poured on 500 g of ice and then filtered to separate the resulting precipitate. The separated precipitate was dried in atmosphere, suspended in ethanol and then heated for 30 minutes in water bath. The reaction solution was allowed to stand at room temperature to obtain 28.6 g (Yield: 90%) of the desired 2,3-dichloro-1,4-naphthoquinone.

(2) In a 200 ml round bottom flask, 1 g of 2,3-dichloro-1,4-naphthoquinone obtained in the above (1) was dissolved in 50 ml of 95% aqueous ethanol solution, and then 0.70 g of 4-cyanoaniline was added thereto. This reaction mixture was allowed to react by heating for 3 hours under reflux. After the completion of the reaction is identified by thin layer chromatography, the reaction solution was cooled down to precipitate the crystal which was filtered and purified by recrystallization from ethanol to obtain 0.84 g (Yield: 62%) of the desired title compound in the form of a reddish-yellow plate.

Melting Point: 188°–189° C.

IR(KBr, $cm^{-1}$): 3230(s, NH), 3050, 2955, 2250(s, CN), 1680(s, C=O), 1640, 1515, 880, 710

$^1$H-NMR($CDCl_3$): δ ppm=1.59(1H, NH), 2.3(2H, q, $CH_2$, J=7.3 Hz, 7.4–8.5(8H, m, aromatic)

EXAMPLE 2

Preparation of 2-chloro-3-[(5-methylpyridin-2-yl)-amino]-1,4-naphthoquinone

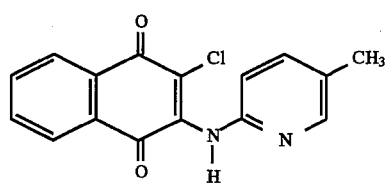

The same procedure as Example 1-(2), except that 0.5 g of 2-amino-5-methylpyridine, instead of 4-cyanoaniline, was used to react for 5 hours, was conducted to obtain 0.99 g (Yield: 76%) of the desired title compound in the form of a reddish-yellow plate.

Melting Point: 260–261° C.

IR(KBr, $cm^{-1}$): 3220(s, NH), 3025, 1680(s, C=O), 1640, 1515, 880, 810

$^1$H-NMR(CDCl$_3$/DMSO-d$_6$): δ ppm=1.59(1H, NH), 1.9 (3H, s, CH$_3$), 7.3–7.8(4H, m, aromatic), 8.1–8.4(3H, m, pyridine ring)

The inhibitory activity of the 2-chloro-3-arylamino-1,4-naphthoquinone derivative of formula (I) according to the present invention against platelet aggregation was demonstrated by the following experiments. In the following experiments, 2-chloro-3-[(4-cyanophenyl)-amino]-1,4-naphthoquinone (hereinafter referred to as "NQ-Y15") prepared in the above Example 1 was used as the compound according to the present invention.

Experiment 1

Determination of Inhibitory Activity Against Platelet Aggregation Induced by Platelet Agonists (1) Preparation of platelet rich plasma and washed platelet:

Blood was taken from abdominal aorta of rat using a syringe in which sodium citrate (final content 0.38%) was previously filled, and centrifuged under 160×g at room temperature for 15 minutes to obtain the platelet rich plasma as the supernatant. This platelet rich plasma was centrifuged again under 1500×g for 15 minutes to obtain the precipitate which was then washed three times with a washing buffer solution (129 mM sodium chloride, 0.8 mM dipotassium hydrogenphosphate, 8.9 mM sodium carbonate, 2.8 mM potassium chloride, 0.8 mM magnesium chloride, 5.6 mM glucose, 10 mM N-[2-hydroxyethyl]-piperazine-N'-[2-ethanesulfonic acid], acidity pH 7.4) containing 2 mM ethylenediamine tetraacetic acid to remove protein and calcium from the plasma. This plasma was then carefully re-suspended in a modified Tyrode's buffer solution (129 mM sodium chloride, 0.8 mM dipotassium hydrogenphosphate, 8.9 mM sodium carbonate, 2.8 mM potassium chloride, 0.8 mM magnesium chloride, 5.6 mM glucose, 10 mM N-[2-hydroxyethyl]piperazine-N'-[2-ethanesulfonic acid], acidity pH 7.4) containing 0.35% bovine serum albumin to obtain the washed platelet.

(2) Determination of platelet aggregation ability:

In this experiment, the platelet aggregation ability was determined by measuring a change in light transmission depending on turbidity change by means of an apparatus for measuring platelet aggregation ability (Chronolog Co.: Pennsylvania, Harvertown) according to a method of Born (see, Born, G. V. R., Nature, 194, 927, 1962). As the control, the light transmission degree for the plasma having substantially no platelet was used. 495 μl of the platelet rich plasma prepared in the above (1) was added to a cuvette for aggregometer, which has a silicon-treated surface. This cuvette was pre-treated by inserting it into a cuvette channel which is maintained at 37° C. and retaining for 30 seconds. Then, 2.5 μl of the compound according to the present invention, NQ-Y15 (final concentration 10$^{-4}$M), dissolved in dimethylsulfoxide was added to the cuvette. The reaction was conducted again at 37° C. for 8 minutes. Then, the change in light transmission developed by adding 2.5 μl of thrombin (final concentration 0.5U/ml) thereto was measured for 10 minutes.

In addition, 495 μl of the washed platelet prepared in the above (1) was pre-treated for 30 seconds at 37° C. according to the same procedure as above and then 2.5 μl of the compound according to the present invention, NQ-Y15, dissolved in dimethylsulfoxide was added thereto. This mixture was allowed to react for 8 minutes at 37° C. Then, 2.5 μl of the platelet agonist (thrombin 0.1U/ml, collagen 10 μg/ml or calcium ionophore A23187 having the following formula 2 μM) was added to the reaction mixture to induce the platelet aggregation and then the change in light transmission was measured for 10 minutes. In this experiment, the light transmission degree for Tyrode's buffer solution was used as the control.

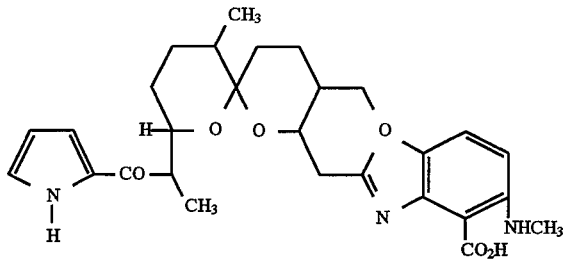

[Calcium ionophore A23187]

The result was determined by calculating the relative ratio of the light transmission degree obtained in each case to the light transmission degree obtained from treatment only with platelet agonists, which is regarded as 100% aggregation.

Figure 1:
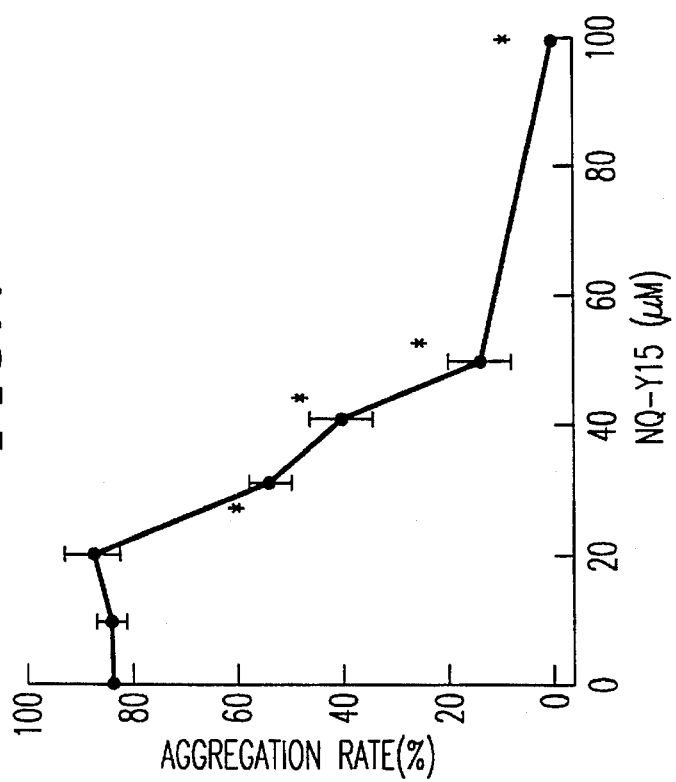
FIG. 1 is a graph showing the inhibitory activity of the compound (NQ-Y15) according to the present invention against platelet aggregation activated by thrombin.
Figure 3:
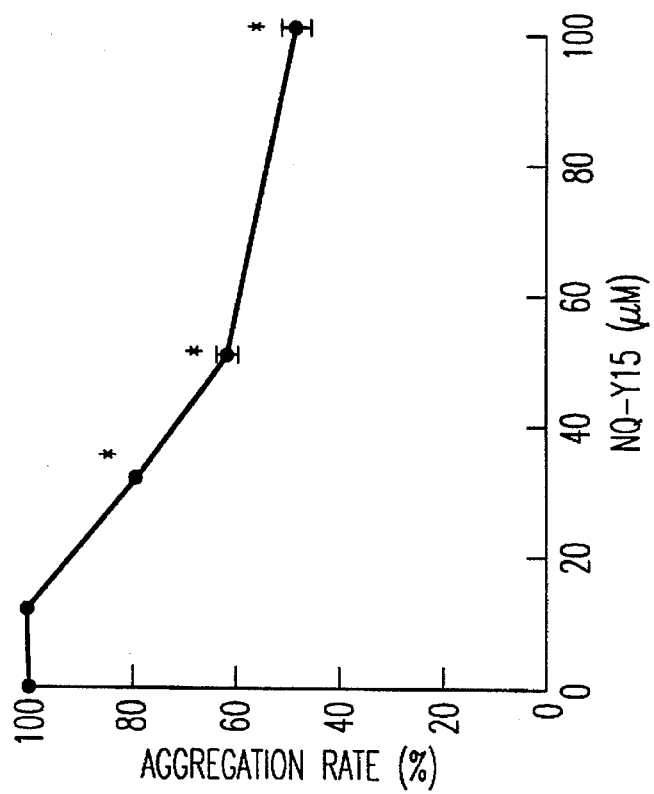
FIG. 3 is a graph showing the inhibitory activity of the compound (NQ-Y15) according to the present invention against platelet aggregation activated by A23187.

The results obtained above are shown in FIGS. 1 to 3. As can be seen from the result depicted in FIGS. 1 to 3, the activity of the compound according to the present invention, NQ-Y15, against the washed platelet aggregation induced by platelet agonists, i.e. thrombin, collagen and A23187 are dependent upon the concentration of NQ-Y15. Specifically, the concentration of NQ-Y15 by which the platelet aggregation induced by agonists is reduced by 50% was measured as about 38 μM for thrombin (0.1U/ml) (FIG. 1), about 7 μM for collagen (10 μg/ml) (FIG. 2) and about 100 μM for A23187 (2 μM) (FIG. 3). Accordingly, it could be identified that the compound according to the present invention inhibits the platelet aggregation induced by platelet agonists dependent upon its concentration.

Experiment 2

Determination of Inhibitory Activity Against 5-[$^{14}$C]-serotonin Secretion

Contrary to other cells, platelets contain numerous granules such as dense granule, α-granule, lysosome and peroxisome, each of which preserves very useful physiological substances. When platelet is activated by any stimulus, substances contained in granules are secreted out of the cells through exocytosis. Particularly, dense granule contains adenine nucleotides such as adenosine diphosphate (ADP), adenosine triphosphate (ATP), etc, calcium, serotonin, etc., which are secreted upon aggregation of platelets and then cause irreversible secondary aggregation. Thus, it can be said that irreversible secondary aggregation induced by ADP, thrombin, etc. is the result of such granule secretion. Accordingly, the following experiment was conducted to identify the inhibitory activity of the compound according to the present invention against platelet aggregation by measuring the effect of the compound of the present invention on secretion of serotonin as one of such physiologically active substances.

The inhibitory activity of the compound of the present invention against serotonin secretion was determined using [$^{14}$C]-serotonin-loaded platelet according to the method of Huzoor, et. al. (see, Huzoor-Akbar, Patel, S., Kokrady, S., Witiak, D. T., Newman, H. A. I. and Feller, D. R., Biochem. Pharmacol. 30, 2013–2020, 1981). Specifically, 5-[$^{14}$C]-serotonin was added to the washed platelet. This mixture was incubated for 30 minutes at 37° C., washed with a washing buffer solution (129 mM sodium chloride, 0.8 mM dipotassium hydrogenphosphate, 8.9 mM sodium carbonate, 2.8 mM potassium chloride, 0.8 mM magnesium chloride, 5.6 mM glucose, 10 mM N-[2-hydroxyethyl]-piperazine-N'-[2-ethanesulfonic acid], acidity pH 7.4), and then re-suspended in a modified Tyrode's buffer solution (129 mM sodium chloride, 0.8 mM dipotassium hydrogenphosphate, 8.9 mM sodium carbonate, 2.8 mM potassium chloride, 0.8 mM magnesium chloride, 5.6 mM glucose, 10 mM N-[2-hydroxyethyl]-piperazine-N'-[2-ethanesulfonic acid], acidity pH 7.4) containing 0.35% bovine serum albumin to adjust the number of cells. Then, 2 µM imipramine was added to the suspension to block the re-absorption of serotonin. After adding the compound of the present invention, NQ-Y15, the mixture was reacted for 8 minutes at 37° C. and then the platelet agonist (thrombin or collagen) was added thereto. The reaction was allowed to stop by adding 4 mM ethylenediamine tetraacetic acid and 10 mM formaldehyde. This mixture was then centrifuged under 12,000×g at room temperature for 2 minutes to separate the supernatant from which the radioactivity of 5-[$^{14}$C]-serotonin was measured. The obtained result are shown in FIGS. 4 and 5.

Figure 4:
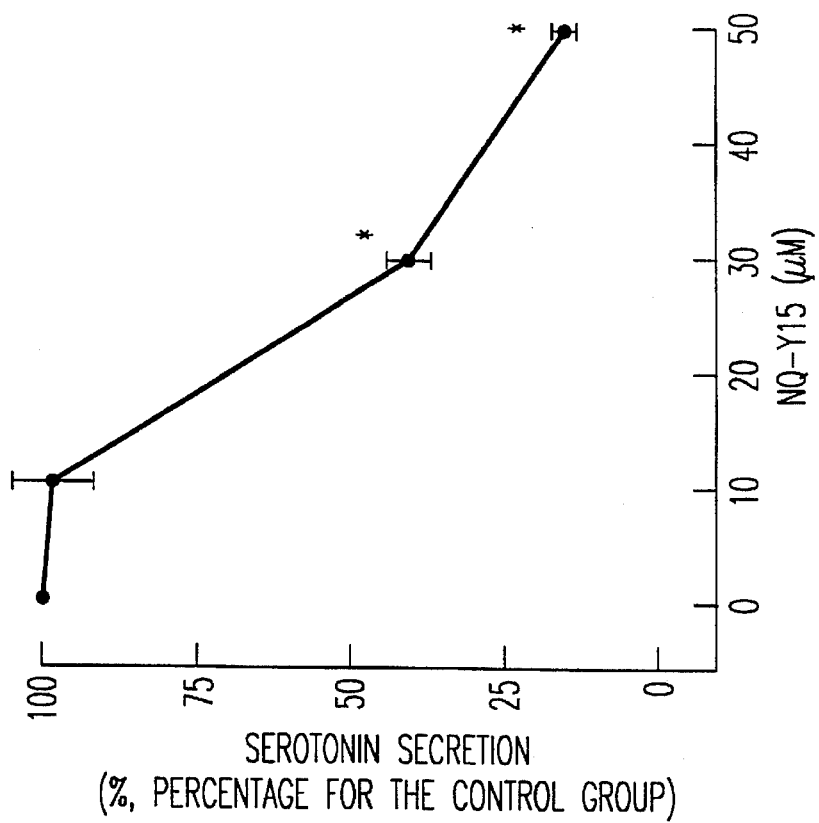
FIG. 4 is a graph showing the inhibitory activity of the compound (NQ-Y15) according to the present invention against intragranular serotonin secretion induced by thrombin.
Figure 5:
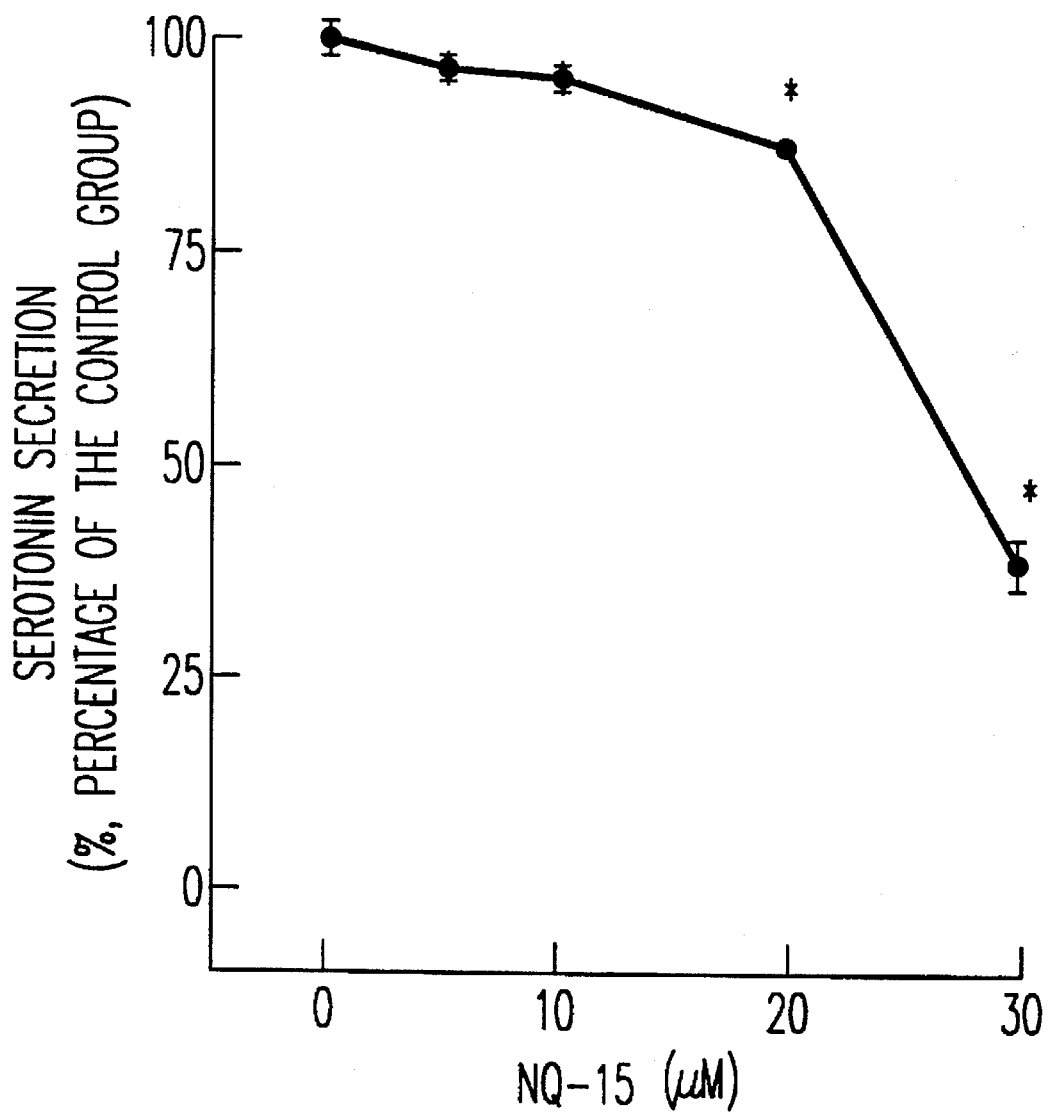
FIG. 5 is a graph showing the inhibitory activity of the compound (NQ-Y15) according to the present invention against intragranular serotonin secretion induced by collagen.

From the result depicted in FIGS. 4 and 5, as can also be identified from FIGS. 1 and 2, it could be seen that the compound of the present invention, NQ-Y15, inhibits the serotonin secretion increased by thrombin (FIG. 4) and collagen (FIG. 5) within the range of concentration capable of inhibiting platelet aggregation induced by platelet agonists. Accordingly, it could be concluded that the compound according to the present invention can reduce the platelet aggregation ability through a mechanism of inhibiting the secretion of substances increasing aggregation from dense granules in activated platelet.

Experiment 3

Determination of Inhibitory Activity Against Production of Thromboxane $A_2$

The ability of producing thromboxane $A_2$ was determined as follow according to the method described in literature [see, Ko, F. N., Sheu, S. J., Liu, Y. M., Huang, T. F., and Teng, C. M., Inhibition of rabbit platelet aggregation by 1,4-naphthoquinones, Thromb. Res. 57, 453–463, 1990]. The experiment was conducted in a plastic cuvette containing 0.5 ml of the washed platelet ($3\times10^8$ platelet/ml) while maintaining the temperature at 37° C. First, the washed platelet was pre-treated with the compound of the present invention, NQ-Y15, for 8 minutes and then collagen was added thereto. After incubation for 5 minutes, the reaction was allowed to stop by adding 2 mM ethylenediamine tetraacetic acid and 50 µM indomethacin. This mixture was centrifuged under 12,000×g at room temperature for 2 minutes to separate the supernatant which was then stored at −20° C. Since thromboxane $A_2$ has a unstable structure and therefore, is immediately converted into a stable thromboxane $B_2$, the production of thromboxane $B_2$ as an index for the thromboxane $A_2$ production was measured by radioimmunoassay. The obtained result is described in the following Table 1.

TABLE 1

Inhibitory activity of NQ-Y15 against thromboxane $B_2$ synthesis

| Experimental condition | Thromboxane $B_2$ (ng/ml) |
| --- | --- |
| Solvent (DMSO) + physiological saline | 0.82 ± 0.22 |
| Solvent (DMSO) + collagen | 98.44 ± 11.52 |
| NQ-Y15 (50 µM) + collagen | 8.50 ± 1.81 |
| NQ-Y15 (30 µM) + collagen | 15.30 ± 2.84 |
| NQ-Y15 (10 µM) + collagen | 78.33 ± 11.85 |

Note: DMSO = dimethylsulfoxide

As can be seen from the result described in the above Table 1, NQ-Y15 according to the present invention showed a significant inhibitory effect of 86.35% and 15.54% at the concentration of 50 µM and 30 µM, respectively, on the increase in thromboxane $A_2$ production induced by collagen treatment. Accordingly, it could be concluded that the compound according to the present invention attributes to the inhibition of platelet aggregation through a mechanism of inhibiting the production of thromboxane $A_2$ which is secreted from activated platelet and accelerates the activation of platelets.

Experiment 4

Test for Excretion of Lactic Acid Dehydrogenase

Lactic acid dehydrogenase (LDH) is an enzyme present in cytoplasm of platelets and is excreted from platelet cytoplasm into extracellular fluid when platelet membrane is injured or cytotoxicity such as cytolysis is induced. Accordingly, it was intended to identify whether the compound of the present invention induces the cytotoxicity by quantitatively measuring lactic acid dehydrogenase excreted after the pre-treatment with the compound of the present invention.

To the washed platelet, dimethylsulfoxide(DMSO) (control group) which can dissolve the compound, NQ-Y15, of the present invention, NQ-Y15 or Triton X-100 (0.1%) which can disrupt the cellular membrane was added. Then, this mixture was centrifuged under 12,000×g at room temperature for 2 minutes to separate the supernatant. To the separated supernatant was added a reagent for measuring lactic acid dehydrogenase LD-L10$^R$ (Sigma) and then the excreted lactic acid dehydrogenase was quantitatively analyzed by means of an automated clinical chemistry analyzer SBA300 (Gilford) which can automatically quantitate lactic acid dehydrogenase. The obtained result is described in the following Table 2.

TABLE 2

Effect of the compound of the present invention (NQ-Y15) on the excretion of lactic acid dehydrogenase from platelets

| | Concentration of LDH (U/L) | | |
| --- | --- | --- | --- |
| Time (min.) | Solvent only (DMSO) | NQ-Y15 (0.1 mM) | Triton X-100 (0.1%) |
| 0 | 6.13 ± 1.13 | 2.87 ± 0.12 | 426.40 ± 9.64 |
| 10 | 5.73 ± 2.54 | 4.57 ± 1.05 | 443.07 ± 1.27 |
| 20 | 8.25 ± 1.85 | 5.47 ± 0.52 | 444.93 ± 4.97 |
| 40 | 9.77 ± 1.37 | 8.47 ± 0.43 | 442.20 ± 0.87 |
| 80 | 12.20 ± 1.74 | 11.55 ± 0.05 | 443.73 ± 0.37 |
| 120 | 14.83 ± 1.39 | 16.67 ± 1.24 | 443.30 ± 2.53 |

As can be seen from the result described in the above Table 2, the compound of the present invention, NQ-Y15 does not show any significant difference from the control group even in the case that the platelet is pre-treated for 120 minutes at the concentration of 0.1 mM which is the concentration to completely inhibit the platelet aggregation. Accordingly, it could be identified that the present compound NQ-Y15 does not cause a cytotoxicity even at high concentration.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A 2-chloro-3-arylamino-1,4-naphthoquinone derivative represented by the following formula (I):

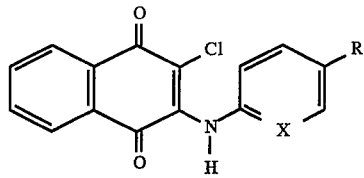

in which

X represents nitrogen (N) or carbon (C) atom and

R represents cyano, or

R can further represent alkyl, carboxyl or acyl when X represents nitrogen (N) atom.

2. The compound of formula (I) as defined in claim 1, wherein X represents nitrogen or carbon atom and R represents cyano, or X represents nitrogen atom and R represents lower alkyl having 1 to 6 carbon atoms, carboxyl or alkylcarbonyl having 1 to 6 carbon atoms in alkyl moiety.

3. The compound of formula (I) as defined in claim 2, wherein X represents nitrogen or carbon atom and R represents cyano, or X represents nitrogen atom and R represents methyl, carboxyl or acetyl.

4. The compound of formula (I) as defined in claim 1, wherein the compound is selected from the group consisting of 2-chloro-3-[(4-cyanophenyl)-amino]-1,4-naphthoquinone and 2-chloro-3-[(5-methylpyridin-2-yl)-amino]-1,4-naphthoquinone.

5. A process for preparing a 2-chloro-3-arylamino-1,4-naphthoquinone derivative represented by the following formula (I):

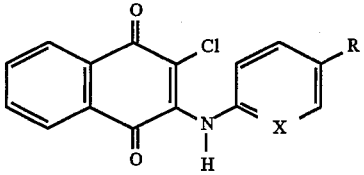

in which

X represents nitrogen (N) or carbon (C) atom and

R represents cyano, or

R can further represent alkyl, carboxyl or acyl when X represents nitrogen (N) atom, characterized in that 2,3-dichloro-1,4-naphthoquinone represented by the following formula (II):

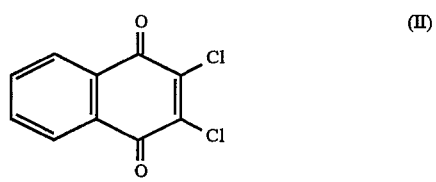

is reacted with an arylamine represented by the following formula (III):

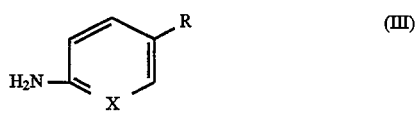

wherein X and R are defined as above.

6. The process as defined in claim 5, characterized in that the reaction is carried out in the presence of an alcohol solvent.

7. The process as defined in claim 6, characterized in that the alcohol solvent is ethanol.

8. The process as defined in claim 5, characterized in that the reaction is carried out at room temperature to 100° C.

9. The process as defined in claim 5, characterized in that the reaction is carried out for 2 to 6 hours.

10. A composition for inhibiting blood coagulation which comprises the 2-chloro-3-arylamino-1,4-naphthoquinone derivative of formula (I) according to claim 1 as an active ingredient together with a pharmaceutically acceptable carrier.

11. A composition for inhibiting blood coagulation which comprises the 2-chloro-3-arylamino-1,4-naphthoquinone derivative of formula (I) according to claim 2 as an active ingredient together with a pharmaceutically acceptable carrier.

12. A composition for inhibiting blood coagulation which comprises the 2-chloro-3-arylamino-1,4-naphthoquinone derivative of formula (I) according to claim 3 as an active ingredient together with a pharmaceutically acceptable carrier.

13. A composition for inhibiting blood coagulation which comprises the 2-chloro-3-arylamino-1,4-naphthoquinone derivative of formula (I) according to claim 4 as an active ingredient together with a pharmaceutically acceptable carrier.

* * * * *